United States Patent [19]

Smith

[11] Patent Number: 4,885,543
[45] Date of Patent: Dec. 5, 1989

[54] ELECTROSTATIC DISCHARGE TEST APPARATUS

[75] Inventor: William C. Smith, Las Cruces, N. Mex.

[73] Assignee: The United States of America as represented by the Administrator of the National Aeronautics and Space Administration, Washington, D.C.

[21] Appl. No.: 156,393

[22] Filed: Feb. 16, 1988

[51] Int. Cl.$^4$ ............................................. G01N 27/60
[52] U.S. Cl. ..................................... 324/452; 324/454; 324/455; 324/72
[58] Field of Search .................. 324/454, 455, 452, 72

[56] References Cited

U.S. PATENT DOCUMENTS

| | | | |
|---|---|---|---|
| 2,421,430 | 6/1947 | Ott | 324/454 |
| 3,225,299 | 12/1965 | Middendorf | 324/160 |
| 3,406,344 | 10/1968 | Hopper | 375/43 |
| 3,544,889 | 12/1970 | Alauzet et al. | 324/455 |
| 3,727,125 | 4/1973 | Mourier | 324/455 |
| 3,943,437 | 3/1976 | Mourier | 324/455 |

FOREIGN PATENT DOCUMENTS

| | | | |
|---|---|---|---|
| 0048550 | 9/1979 | Japan | 324/452 |
| 0571936 | 10/1977 | U.S.S.R. | 324/454 |

OTHER PUBLICATIONS

"Testing of Electrostatic Materials", G. Baumgartner & R. Havermann, Lockheed Missiles & Space Co., Inc., pp. 97–103, Oct. 1984.

"Characterization of ESD Safe Requirements for Floor Surfaces", George Berbeco, President, Charleswater Products, Inc., pp. 124–130, Sep. 1982.

"Triboelectric Testing for Electrostatic Charges on Materials at Kennedy Space Center", Raymond H. Gompf, Professor, pp. 58–63, Oct. 1984.

"An Electrostatic Charge Decay Technique for Nondestructive Evaluation of Nonmetallic Materials", Ming-Kai Tse and Nam P. Suh, Massachusetts Institute of Technology, 1983.

Primary Examiner—Reinhard J. Eisenzopf
Assistant Examiner—Anthony L. Miele

[57] ABSTRACT

Electrostatic discharge properties of materials are quantitatively measured and ranked. Samples (20) are rotated on a turntable (15) beneath selectable, co-available electrostatic chargers (30/40), one being a corona charging element (30) and the other a sample-engaging triboelectric charging element (40). They then pass under a voltage meter (25) to measure the amount of residual charge on the samples (20). After charging is discontinued, measurements are continued to record the charge decay history over time.

12 Claims, 3 Drawing Sheets

ELECTROSTATIC DISCHARGE TEST APPARATUS

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

The present invention relates to a device for measuring electrostatic properties of materials so that the materials can be quantitatively ranked. Determining the electrostatic discharge properties and characteristics of certain materials can be critical in applications involving semiconductors, which are sensitive to static discharge and can be easily ruined by such discharges. Electrostatic discharge properties can also be critical where fluids are used which might be ignited by static discharges. In the aerospace industry, the determination of electrostatic discharge properties of materials can be of critical importance.

Prior art testing methods have been unsatisfactory for several reasons. Typically, they utilize corona charging techniques and provide no concurrent information concerning the triboelectric charging propensities and sensitivities of the materials being tested. Yet to be fully determinative, it is necessary to have information and testing capabilities for both.

Another disadvantage of prior art methods is that they have provided no direct comparison among properties of different materials. The current practice of quoting electrostatic properties in qualitive and unrelated terminology makes application of materials difficult. It is important to be able to rank materials directly with competing materials in use conditions.

In trying to compare different materials using prior art equipment and methods, it has been necessary and critical, but very difficult, to calibrate the voltage sensor, and to maintain accurate environmental controls, since testing has been done on each sample separately. Other prior art disadvantages obtain when sample surface integrity is not preserved.

The traditional methods used for electrostatic discharge tests on materials may roughly be classified as: (1) resistivity tests, (2) shielding tests, (3) discharge tests, and (4) triboelectric tests. Tests which measure volume and surface resistivities include such methods as ASTM D-257 and ASTM D-991. Resistivity tests are both simple and reproducible, but the results of resistivity tests seem to have no simple correlation with electrostatic discharge behavior. Shielding tests, such as ASTM F 365-73T, only measure transient effects, so are too specific to be useful for general characterization of electrostatic behavior. Discharge methods, including ASTM D-4238 and FED STD 101C Method 4046.1, are widely used because they provide direct and sensitive characterizations of electrostatic discharge properties. They characterize the dissipative electrostatic properties of materials, but ignore an important charge generation property of materials, namely, tribocharging. Tribocharging methods include the AATCC Test Method 134-1979 and the KSC Triboelectric Test Method. Both these methods address the generation of charge triboelectrically, but the latter also measures charge decay.

With regard to the patent literature, U.S. Pat. No. 2,421,430 (Ott, issued June 3, 1947) discloses a device for measuring static electricity present in textile materials utilizing the triboelectric method. A rotating plate is featured, but is utilized to impart frictional contact with the material in order to affect the static electrical charge on the material.

U.S. Pat. No. 3,225,299 (Middendorf, issued Dec. 21, 1965) discloses a tachometer for measuring rotational speed by measuring the rate of transfer of electrostatic charge desposited on the dielectric surface of a rotor, from one electrode to another.

U.S. Pat. Nos. 3,727,125 and 3,943,437 (Mourier, issued Apr. 10, 1973, and Mar. 9, 1976) disclose the use of the corona effect to determine discharge properties of materials placed on a rotating plate and alternatively charged and tested for electrical content.

U.S. Pat. No. 3,544,889 (Alauzet et al., issued Dec. 1, 1970) discloses the use of the corona effect to test samples on a rotating plate.

U.S. Pat. No. 3,406,344 (Hopper, issued Oct. 15, 1968) is believed to disclose nothing further than the above.

Non-patent literature of possible interest includes:

Baumgartner, G. and Haverman, R., "Testing of Electrostatic Materials FED. STD. 101C, Method 4046.1", in *Electrical Overstress/Electrostatic Discharge Symposium Proceedings*, pp. 97–103. Philadelphia: The EOS/ESD Association, October, 1984.

Berbeco, George R., "Characterization of ESD Safe Requirements for Floor Surfaces.", in *Electrical Overstress/Electrostatic Discharge Symposium Proceedings*, pp. 124–130. Orlando, Fla.: IIT Research Institute, Sepember, 1982.

Gompf, Raymond H., "Triboelectric Testing for Electrostatic Charge on Materials at Kennedy Space Center.", in *Electrical Overstress/Electrostatic Discharge Symposium Proceedings*, pp. 58–63. Philadelphia: The EOS/ESD Association, October, 1984.

Tse, Ming-Kai and Suh, Nam P., "An Electrostatic Charge Decay Technique for Nondestructive Evaluation of Nonmetallic Materials.", in *International Advances in Nondestructive Testing*, Vol. 9, pp. 193–226. Gordon and Breach, Science Publishers, Inc., n.p., 1983.

A need therefore remains for a method and apparatus for measuring electrostatic properties of materials such that the materials can be easily, accurately, and repeatably ranked quantitatively with respect to both electrostatic charging and triboelectric charging. Further, such a method and apparatus must not be overly sensitive to instrument calibration or environmental control conditions, and must preserve sample surface integrity for determination of tribocharge generation propensity.

SUMMARY OF THE INVENTION

Briefly, the present invention meets the above needs and purposes with a new and improved method and apparatus for measuring the electrostatic discharge characteristics of various materials, in which samples of the materials are simultaneously measured for immediate comparative ranking of their electrostatic discharge properties. Further, not only are multiple samples of different materials measured simultaneously, but the apparatus is provided with on-board electrostatic charging facilities and on-board triboelectric charging facilities, either of which may be easily selected according to the testing to be done.

Accordingly, the present invention overcomes many of the limitations of existing designs by performing both discharge tests and triboelectric tests on the same apparatus for multiple samples simultaneously. Simultaneous testing of multiple samples nullifies many of the variables that cause problems when the electrostatic discharge characteristics of materials are determined and compared separately. A standard test using fixed environmental conditions can thus be easily accommodated using the present invention, yet quick "relative" ranking can be obtained for special situations, with little or no concern for environmental controls.

In the apparatus according to the present invention, multiple sample holders are placed at a specific radius from the center of a rotating turntable. A non-contact, electrostatic voltmeter probe is placed at the sample radius at one end of a diameter, while a charging mechanism is provided at the opposite end. One mechanism is a tribocharging surface that can be engaged with the sample surface for a period of time and then retracted. An alternative mechanism is a corona electrode mounted on a retractable support and connected to an external, high-voltage power supply.

The voltmeter probe, mounted perpendicularly to the plane of the turntable approximately 6 mm above the samples, registers the sample voltage each time a sample passes underneath. The output of the voltmeter is recorded on a fast-responding digital signal acquisition device. When the retractable corona electrode is selected, the electrode is positioned nominally 15 mm above the sample surface. When the tribocharging surface is selected, the surface is lowered to engage the abrading material with the top surface of the sample. During each revolution of the turntable, each sample successively has charge deposited onto it as it passes beneath the selected charging mechanism, and then has its voltage determined as it passes beneath the voltmeter probe. Consequently, the time behavior of the peak voltage corresponding to a given sample is a dynamic measure of the change in charge on the sample surface.

Therefore, in a preferred embodiment, the present invention provides both a method and an apparatus for measuring the electrostatic discharge behavior of a plurality of test samples. Co-available first and second electrostatic charging means for selectably available, one being a corona charging means and the other a triboelectric charging means. One of the electrostatic charging means is then selected and supported for sequentially exposing the plurality of test samples to the selected charging means. For convenience in preparing and handling the samples, individual sample holders or support means are provided for individually supporting the plurality of test samples on the apparatus. The amount of electrostatic charge on the individual samples is then measured by a suitable voltage measuring device supported over the sample holders on the apparatus. The voltage measuring device also monitors the decay of the charge to determine the individual electrostatic discharge behavior of the samples.

A turntable having the sample support holders mounted thereon sequentially moves the support holders and their samples to the selected electrostatic charging means and then to the voltage measuring means, for sequentially exposing the samples on the turntable to the electrostatic charging and then to measuring of the charge. Preferably, the charging means and the measuring means are located substantially opposite one another across the turntable.

Preferably also, the invention includes suitable computer, memory, display, and printer means, as desired, for generating the desired output results, such as graphical displays of the measured electrostatic charge decays.

It is therefore an object of the present invention to provide a new and improved electrostatic discharge test apparatus and method therefor; such a method and apparatus which is particularly well adapted for measuring the electrostatic discharge behavior of a plurality of selected test samples; which is equally and conveniently able to measure both the corona charging and the triboelectric charging behavior of such samples as well as the subsequent discharging behavior of the samples; which includes co-available electrostatic charging means, one being a corona charging means and the other a triboelectric charging means; in which the electrostatic charging means are supported for sequentially exposing the test samples to a selected one of the charging means; in which a measuring means is provided for individually measuring the amount of electrostatic charge on the samples and for monitoring the decay of such charge to determine the individual electrostatic discharge behavior of the samples; and to accomplish the above objects and purposes in an inexpensive, uncomplicated, durable, versatile, and reliable method and apparatus, inexpensive to manufacture, and readily suited to the widest possible utilization in measuring the electrostatic discharge characteristics of various materials.

These and other objects and advantages of the invention will be apparent from the following description, the accompanying drawings, and the appended claims.

DESCRIPTION OF THE PREFERRED EMBODIMENT

Figure 1:
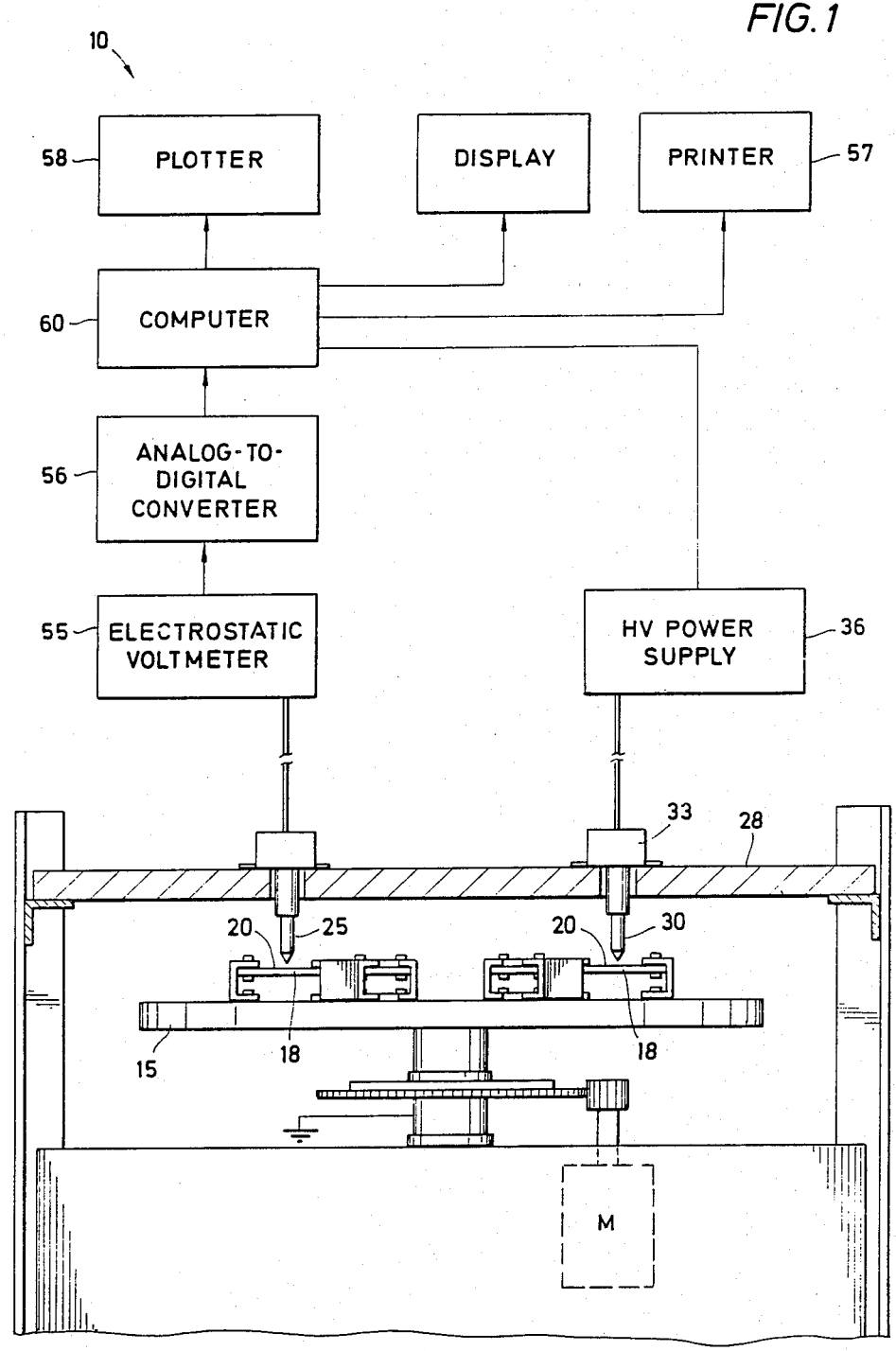
FIG. 1 is a somewhat figurative illustration, partially in elevation and partially in block diagram, showing a preferred embodiment of the invention configured for corona charging measurements.
Figure 2:
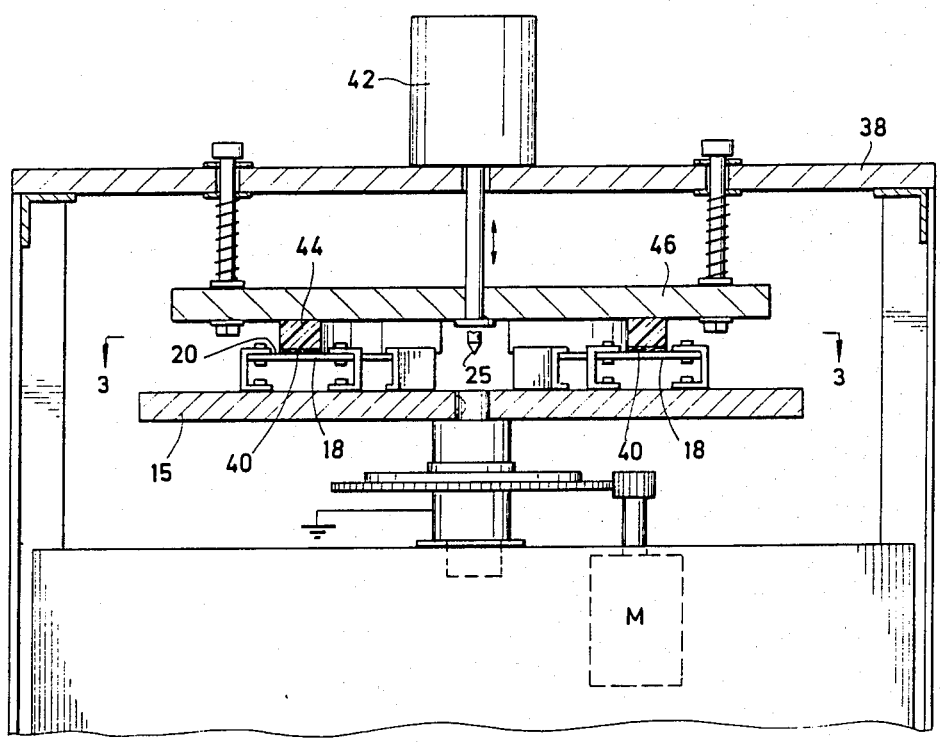
FIG. 2 is a fragmentary, partially sectioned illustration of the FIG. 1 apparatus configured for triboelectric charging measurements.

With reference to the drawings, the new and improved method and apparatus 10 for measuring the electrostatic discharge characteristics of various materials according to the present invention will be described. FIG. 1 shows a preferred embodiment of the invention configured for making such measurements by corona charging the sample materials being tested. FIG. 2 shows the same embodiment configured for making the measurements by triboelectrically charging the sample materials.

Figure 3:
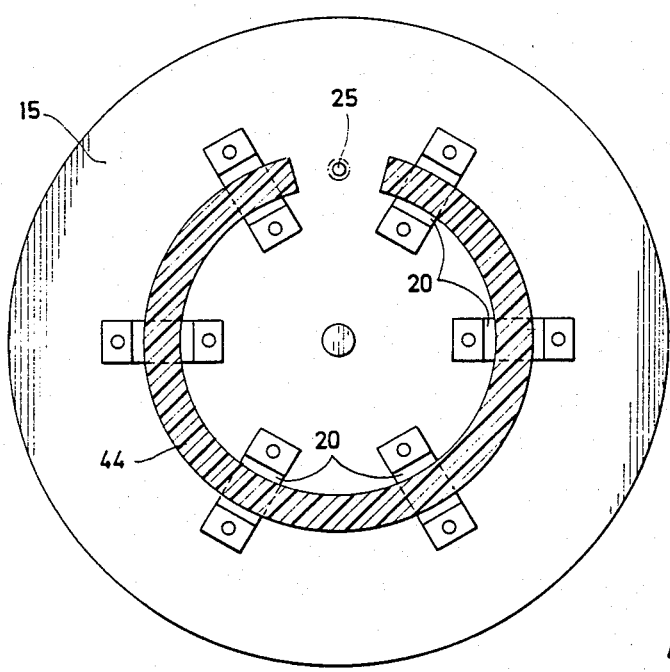
FIG. 3 is a cross-sectional view of the apparatus shown in FIG. 2 taken on line 3—3 in FIG. 2.

At the center of apparatus 10 is a rotating turntable 15 on which multiple sample holders 18 are mounted at a common radius from its center. The sample holders 18 each carry individual samples 20. A non-contact electrostatic voltmeter probe 25 is mounted perpendicular to the plane of the turntable 15 at the same radius as the samples 20, and approximately 6 mm above their surface. At the opposite end of a diameter from the voltmeter probe 25, a charging mechanism is provided. One such mechanism is a corona electrode 30 mounted on a retractable corona support 33 and connected to an external, high-voltage power supply 36. An alternative mechanism is a tribocharging surface 40 that can be lowered into engagement with the sample surface for a period of time and then retracted by retractor 42. Surface 40 is shaped as an annulus (FIG. 3) and carried on the bottom of a similarly shaped foam backing 44 for controlled contact with the samples 20.

Typical operation of the apparatus involves selecting a charging mechanism 30 or 40, and then depositing charges onto each sample 20 successively as it passes underneath the selected charging mechanism. To select the retractable corona charging mechanism, the mounting platform 28 is installed, and the support 33 with attached electrode 30 is lowered about a hinge (not shown) to position the electrode nominally 15 mm above the sample surfaces. To select the tribocharging mechanism, the mounting platform 38 is installed, and the retractable support 46 is lowered using retractor 42 to engage the tribocharging abrading material with the top surfaces of the samples. One half revolution after being charged, each sample passes successively underneath the electrostatic probe 25 which determines the potential of each charged-sample surface. The output of the electrostatic voltmeter 55 is recorded by a fast-responding analog-to-digital converter 56 as a sequence of pulses, the amplitudes of which correspond to the peak potentials measured on successive sample surfaces. Consequently, the time behavior of the peak potential corresponding to a specific sample is a dynamic measure of the change in the charge residing on the sample surface. The computer system 60 accumulates real-time charge and discharge data as well as maximum voltage buildup characteristics.

Figure 4:
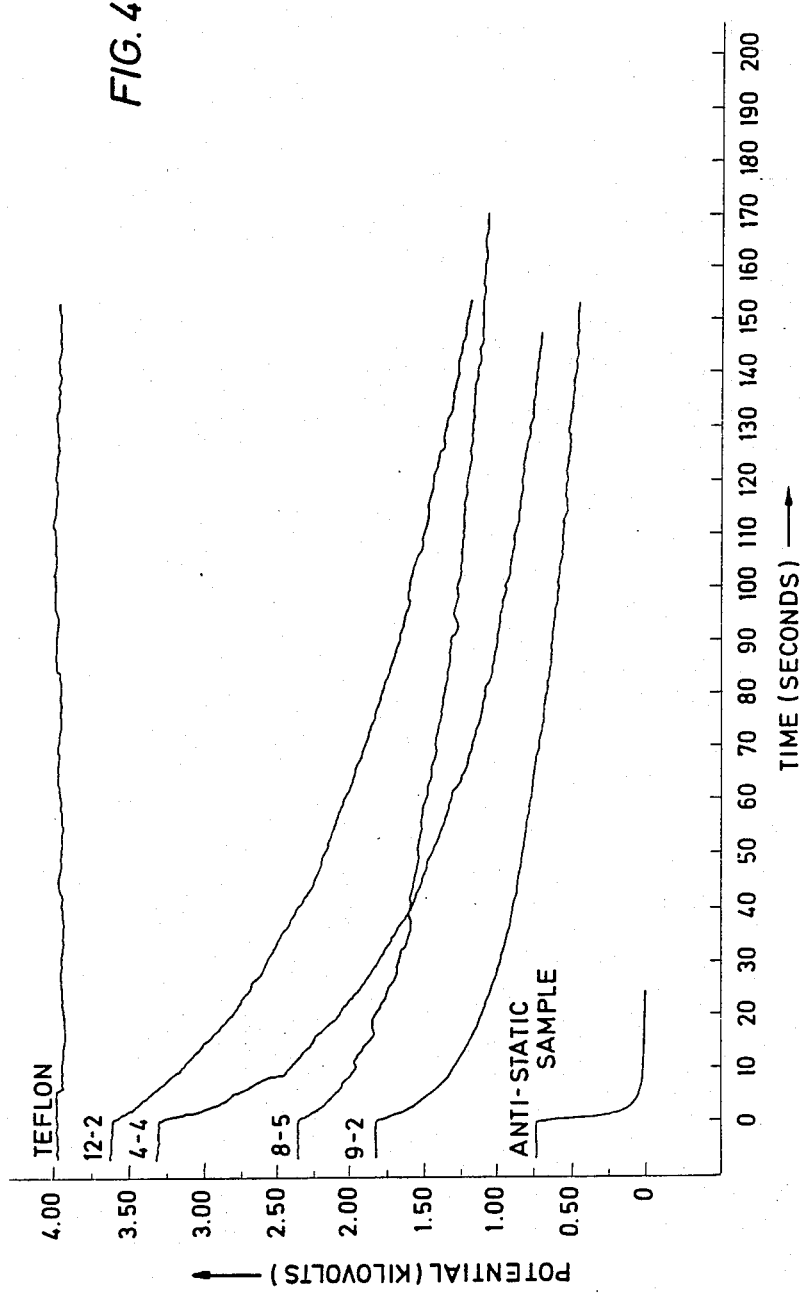
FIG. 4 is a graphical illustration of the electrostatic discharge characteristics of six materials as simultaneously measured by the apparatus illustrated in FIG. 1.

The data plotted in FIG. 4 by plotter 58 were obtained using a Genisco Rate of Turn Table, Model C-181, set at an angular speed of 8.0 radians per second. The angular speed for the Genisco is servo-controlled to be constant within 0.1%, including errors due to wow and drift. Absolute accuracy is within 1.0% of set value. Each setting of the angular speed was constant, and reproduced within 0.01% using a stroboscope.

The curves in FIG. 4 were produced by a computer-plotter interconnection of discrete points. Each point was the value of the peak electrostatic potential recorded as a given charged sample passed underneath the detector probe. Because the samples were affixed at a radius of six inches from the center of the turntable, the time interval between individual points making up each curve was 0.785 seconds.

The sample charging was accomplished by successive passes under the corona charging mechanism, each pass being a fraction of a revolution. Since samples used to generate the data plotted in the curves were 2.0 inches wide (tangential to the circular path), each sample was under the charging mechanism for about 42 milliseconds per revolution. That is to say, a given sample was successively charged for about 42 milliseconds at a time interval of 785 milliseconds. Under the action of these charging "bursts", all materials tested achieved an equilibrium potential in fewer than 150 seconds. Charging behavior was observed to be essentially the same over a range of angular speed from 0.2 radians per second to 20 radians per second. The speed limitations appeared to be (1) detector response time, and (2) "wind" charging. Advantageously, all these data were determined simultaneously on the apparatus, so that identical environmental conditions were assured for all sample materials. Relative electrostatic discharge behavior is thus immediately apparent.

Four of the six curves in FIG. 4 show the electrostatic discharge characteristics of selected paint coatings tested using the configuration of the apparatus shown in FIG. 1. Time (FIG. 4) is measured from the instant charging ceases, which is shown as zero on this graph. To place these traces in perspective, the trace from a one-sixteenth-inch-thick Teflon (TFE) sample is also shown, along with that from a "pink poly" anti-static bag (Maine Poly Inc., MPAS-100T anti-static polyethylene film). The Teflon discharged imperceptibly during the test; the anti-static sample discharged to essentially zero potential in fewer than five seconds. The electrostatic discharge behavior of these paint samples illustrates some of the information that may be extracted from these tests. The maximum potential to which the samples charge primarily depends on two parameters: it is directly related to the sample thickness, and inversely related to the discharge rate. The shape of the curves is roughly fit by a sum of two or more exponentials, each with a different discharge rate coefficient. The occurrence of multiple exponentials supports the suggestion that several discharge mechanisms are simultaneously active for most materials (Tse and Suh 1983).

The apparatus thus permits particularly simple electrostatic charge decay measurements to be made after charging materials with a high-voltage corona electrode. It appeears that electrostatic decay measurements made in this manner may be less subject to measurement-to-measurement variation than those using tribocharging. The corona measurements also appear to be extremely sensitive to variations in material composition. Also, the corona method is a nondestructive test for delicate samples, while the rubbing action required to generate tribocharge can alter the test specimen significantly. With the present invention, therefore, the choice is presented to perform either or both tests as may be desired according to the conditions at hand.

As may be seen, therefore, the present invention has numerous advantages. Simultaneous measurment of multiple samples permits some direct measurements not provided by other electrostatic discharge test systems. The present invention provides a simultaneous direct ranking of the electrostatic discharge properties of several materials in essentially real time. Alternatively, materials with unknown electrostatic discharge properties can be compared directly and quickly to "reference" materials with established electrostatic properties. The anti-static and Teflon samples illustrated in FIG. 4 served as such references, for example. Adaptation of the invention to a standardized method with environmental control is easily attainable, since long term stability of the control is significantly relaxed by the speed with which relative data can be acquired.

The simplicity of the test and the ease with which it can be performed thus indicate that the invention can fulfill the need for such a standard electrostatic discharge test method. In one instance, for example, replacement gloves were evaluated for use by technicians who handle precision-cleaned components. Many Teflon gloves now in use have undesirable limitations, one of the most serious being the tendency of the gloves to contaminate hardware because of electrostatic attraction of particulate material. That is, the gloves exhibit undesirable electrostatic discharge characteristics. Several promising replacements for the gloves were found but no information could be found on the electrostatic discharge properties of the materials. Using the present invention, a test was performed simultaneously on all materials within an hour. Some of the materials were quickly eliminated due to poor electrostatic discharge characteristics.

Unique investigations which can be performed with the apparatus include:

Comparison of tribocharging with corona charging techniques. Corona charging, a nondestructive test, has definite advantages, yet whether corona charging will provide the same data as tribocharging is not certain in every case.

Determination of the relationship between material resistivity measurements and discharge measurements. The simplicity and reproducibility of the resistivity measurements makes their use attractive, but there are questions about their correlation with results of discharge and triboelectric measurements.

Determination of the contribution of individual layers of multilayer coatings to charge buildup and decay. Environmental protection for aerospace launch structure surfaces is usually provided by multilayer paint coatings. Both the coating composition and the method of application can influence the electrostatic discharge properties of the coatings.

Evaluation of the effect of propellants on the electrostatic discharge properties of materials. Spills of liquid or gaseous propellants onto coated surfaces could significantly alter the electrostatic discharge properties of the materials and thereby change hazard conditions.

Evaluation of the effect of vacuum on the electrostatic discharge properties of materials. It appears that little work has been done to establish the electrostatic discharge properties of materials in the near vacuum of extra-vehicular space. Hazard scenarios in space are quite different from those encountered terrestrially.

Comparison of results with this method and apparatus to those obtained by prior art techniques.

Finally, the ability to test the actual material on its use substrate in a simulated use environment is very appealing since the method allows for direct observation of material behavior. For example, the ignition characteristics of solid rocket propellants by electrostatic discharge can be evaluated at selected values of temperature and humidity using the actual material and substrate while observing the ignition event.

While the methods and forms of apparatus herein described constitute preferred embodiments of this invention, it is to be understood that the invention is not limited to these precise methods and forms of apparatus, and that changes may be made therein without departing from the scope of the invention.

What is claimed is:

1. Apparatus for measuring the electrostatic discharge behavior of a plurality of test samples, comprising:
   (a) co-available first and second electrostatic charging means, said first charging means being a corona charging means and said second charging means being a triboelectric charging means,
   (b) means supporting said electrostatic charging means for sequentially exposing such a plurality of test samples to a selected one of said electrostatic charging means, and
   (c) measuring means for individually measuring the amount of electrostatic charge on the samples and for monitoring the decay of such charge to determine the individual electrostatic discharge behavior of the samples.

2. The apparatus of claim 1 further comprising:
   (a) individual sample support means for individually supporting a plurality of such test samples on said apparatus, and
   (b) moving means for sequentially moving said support means and the samples thereon to the selected said electrostatic charging means and then to said measuring means, for sequentially exposing the samples on said support means to the selected said electrostatic charging means and then to said measuring means.

3. The apparatus of claim 2 wherein said moving means further comprises a turntable, and wherein said sample support means are mounted upon said turntable.

4. The apparatus of claim 1 further comprising means for generating a graphical display of the measured electrostatic charge decay.

5. Apparatus for measuring the electrostatic discharge behavior of a plurality of test samples, comprising:
   (a) co-available first and second electrostatic charging means, said first charging means being a corona charging means and said second charging means being a triboelectric charging means,
   (b) means supporting said electrostatic charging means for sequentially exposing such a plurality of test samples to a selected one of said electrostatic charging means,
   (c) individual sample support means for individually supporting a plurality of such test samples on said apparatus,
   (d) measuring means for individually measuring the amount of electrostatic charge on the samples and for monitoring the decay of such charge to determine the individual electrostatic discharge behavior of the samples,
   (e) a turntable having said sample support means mounted thereon for sequentially moving said support means and the samples thereon to the selected said electrostatic charging means and then to said measuring means, for sequentially exposing the samples on said turntable to the selected said electrostatic charging means and then to said measuring means,
   (f) said charging means and said measuring means being located substantially opposite one another across said turntable, and
   (g) means for generating a graphical display of the measured electrostatic charge decay.

6. A method for measuring the electrostatic discharge behavior of a plurality of test samples, comprising:
   (a) selecting an electrostatic charging means from co-available first and second electrostatic charging means, the first being a corona charging means and the second being a triboelectric charging means,
   (b) sequentially exposing a plurality of such test samples to the selected electrostatic charging means, and
   (c) individually measuring the amount of electrostatic charge on the samples and monitoring the decay of such charge to determine the individual electrostatic discharge behavior of the samples.

7. The method of claim 6 further comprising repeatedly charging the samples by repeatedly exposing them to the selected electrostatic charging means to build up a high, steady-state electrostatic charge thereon, prior to monitoring the decay of the charge thereon.

8. The method of claim 6 further comprising:
   (a) individually supporting the test samples on individual sample support means, and
   (b) sequentially moving the support means and the samples thereon to the selected electrostatic charging means and then measuring the amount of electrostatic charge on the samples.

9. The method of claim 8 wherein said step of sequentially moving the samples further comprises rotating the samples past the charging means on a turntable.

10. The method of claim 6 further comprising sequentially measuring the amount of electrostatic charge on the samples while monitoring the decay of the charge and determining the electrostatic discharge behavior of the samples.

11. The method of claim 6 further comprising generating a graphical display of the measured electrostatic charge decay.

12. A method for measuring the electrostatic discharge behavior of a plurality of test samples, comprising:
   (a) selecting an electrostatic charging means from co-available first and second electrostatic charging means, the first being a corona charging means and the second being a triboelectric charging means,
   (b) individually supporting a plurality of such test samples on individual sample support means,
   (c) sequentially and repeatedly rotating the support means and the samples thereon on a turntable past the selected electrostatic charging means for repeatedly exposing the plurality of test samples to the selected electrostatic charging means to build up a high, steady-state electrostatic charge thereon,
   (d) individually and sequentially measuring the amount of electrostatic charge on the samples and monitoring the decay of such charge to determine the individual electrostatic discharge behavior of the samples, said measuring being substantially opposite the electrostatic charging means across the turntable, and
   (d) generating a graphical display of the measured electrostatic charge decay.

* * * * *